(12) United States Patent
Wong et al.

(10) Patent No.: US 9,833,784 B2
(45) Date of Patent: Dec. 5, 2017

(54) FEED BAG CONSTRUCTION

(75) Inventors: Dennis Wong, Dedham, MA (US);
Elias Noukas, Burlington, MA (US);
Kristin Prescott, Billerica, MA (US);
Brian Pereira, Derry, NH (US); John Saragosa, Melrose, NH (US)

(73) Assignee: EMD Millipore Corporation, Burlington, MA (US)

( * ) Notice: Subject to any disclaimer, the term of this patent is extended or adjusted under 35 U.S.C. 154(b) by 32 days.

(21) Appl. No.: 12/818,754

(22) Filed: Jun. 18, 2010

(65) Prior Publication Data
US 2011/0085746 A1 Apr. 14, 2011

Related U.S. Application Data

(60) Provisional application No. 61/283,930, filed on Dec. 9, 2009, provisional application No. 61/271,667, filed on Jul. 24, 2009.

(51) Int. Cl.
*B65D 33/00* (2006.01)
*B01L 3/00* (2006.01)
*C12M 1/00* (2006.01)

(52) U.S. Cl.
CPC ............. *B01L 3/523* (2013.01); *B65D 33/00* (2013.01); *C12M 99/00* (2013.01); *B01L 3/502* (2013.01); *B01L 3/505* (2013.01); *B01L 2200/0689* (2013.01); *B01L 2200/087* (2013.01); *B01L 2300/042* (2013.01); *B01L 2400/0633* (2013.01)

(58) Field of Classification Search
CPC B08B 9/00; B08B 9/08; B08B 9/0804; B08B 9/0813; B08B 9/093; B08B 9/0933; B08B 9/0936; B65D 90/0093; B65D 31/16; B65D 31/18; B65D 75/5861; B65D 75/5866; B65D 75/5872; B65D 75/5883; B65D 88/28; A61F 5/442; A21C 15/005
USPC ......... 383/42, 904; 239/106, 110; 134/22.11, 134/22.12, 22.18, 167 R, 166 R, 170
See application file for complete search history.

(56) References Cited

U.S. PATENT DOCUMENTS 1,182,449 A * 5/1916 Booth ................... B65D 33/24
383/36
1,224,959 A * 5/1917 Rosenfeld ..................... 251/286
(Continued)

FOREIGN PATENT DOCUMENTS

AU 11407/83 A 8/1983
DE 3735257 A1 4/1989
(Continued)

OTHER PUBLICATIONS

International Search Report and Written Opinion received for PCT Patent Application No. PCT/US2010/001768, dated Mar. 25, 2011, 15 pages.
(Continued)

*Primary Examiner* — Jes F Pascua
*Assistant Examiner* — Nina Attel
(74) *Attorney, Agent, or Firm* — EMD Millipore Corporation

(57) ABSTRACT

A feed bag construction is provided comprising a feed bag, a first conduit sealed to the feed bag, a second conduit sealed to the interior of the feed bag for supplying wash reagent to the feed bag and a one piece cap that is removably mounted on the first conduit. The first conduit is provided with a hand operated butterfly valve to open or close the conduit.

2 Claims, 4 Drawing Sheets

(56) References Cited

U.S. PATENT DOCUMENTS

| | | | | |
|---|---|---|---|---|
| 3,186,625 | A * | 6/1965 | McAd | B65D 85/80 383/200 |
| 3,567,120 | A * | 3/1971 | Suda | 239/8 |
| 3,746,001 | A | 7/1973 | Ralston, Jr. | |
| 3,945,534 | A | 3/1976 | Ady | |
| 3,985,266 | A | 10/1976 | Wright, Jr. | |
| 4,428,395 | A * | 1/1984 | Bravo | B65D 55/14 137/364 |
| 4,654,037 | A * | 3/1987 | Fenton | 604/334 |
| 4,792,060 | A | 12/1988 | Brogli | |
| 4,964,185 | A | 10/1990 | Lehn | |
| 4,997,000 | A * | 3/1991 | Feast et al. | 134/170 |
| 5,008,083 | A * | 4/1991 | Dickie et al. | 422/533 |
| 5,078,699 | A | 1/1992 | Haber et al. | |
| 5,219,103 | A | 6/1993 | Carper | |
| 5,341,307 | A | 8/1994 | Myhre et al. | |
| 5,350,089 | A | 9/1994 | Preiser et al. | |
| 5,599,099 | A | 2/1997 | Bullivant | |
| 5,941,635 | A | 8/1999 | Stewart | |
| 6,224,581 | B1 * | 5/2001 | Withers et al. | 604/334 |
| 6,532,971 | B2 * | 3/2003 | Deecki | 134/22.18 |
| 6,702,152 | B1 | 3/2004 | Ludescher | |
| 6,722,631 | B2 * | 4/2004 | Bailey | 251/251 |
| 7,322,969 | B2 * | 1/2008 | Hattori et al. | 604/406 |
| 7,449,327 | B2 | 11/2008 | House et al. | |
| 7,520,407 | B2 | 4/2009 | Crosby et al. | |
| 2003/0080140 | A1 | 5/2003 | Neas et al. | |
| 2003/0198406 | A1 | 10/2003 | Bibbo et al. | |
| 2003/0205277 | A1 * | 11/2003 | Raftis et al. | 137/592 |
| 2004/0154984 | A1 | 8/2004 | Dafny et al. | |
| 2004/0173439 | A1 | 9/2004 | Abdel-Hadi et al. | |
| 2006/0111682 | A1 * | 5/2006 | Schena et al. | 604/334 |
| 2006/0252145 | A1 | 11/2006 | House et al. | |
| 2007/0026102 | A1 | 2/2007 | Devos et al. | |
| 2007/0194042 | A1 | 8/2007 | Wilbur | |
| 2008/0031082 | A1 | 2/2008 | Zambaux | |

FOREIGN PATENT DOCUMENTS

| | | | |
|---|---|---|---|
| DE | 4403755 A1 | 11/1994 | |
| EP | 1602715 A2 * | 12/2005 | C12M 1/00 |
| GB | 1431065 | 4/1976 | |
| WO | 1990/003775 A1 | 4/1990 | |

OTHER PUBLICATIONS

International Preliminary Report on Patentability received for PCT Patent Application No. PCT/US2010/001768, dated Feb. 2, 2012, 11 pages.

Invitation to Pay Additional Fees and Partial International Search Report received for PCT Patent Application No. PCT/US2010/001768, dated Dec. 28, 2010, 7 pages.

* cited by examiner

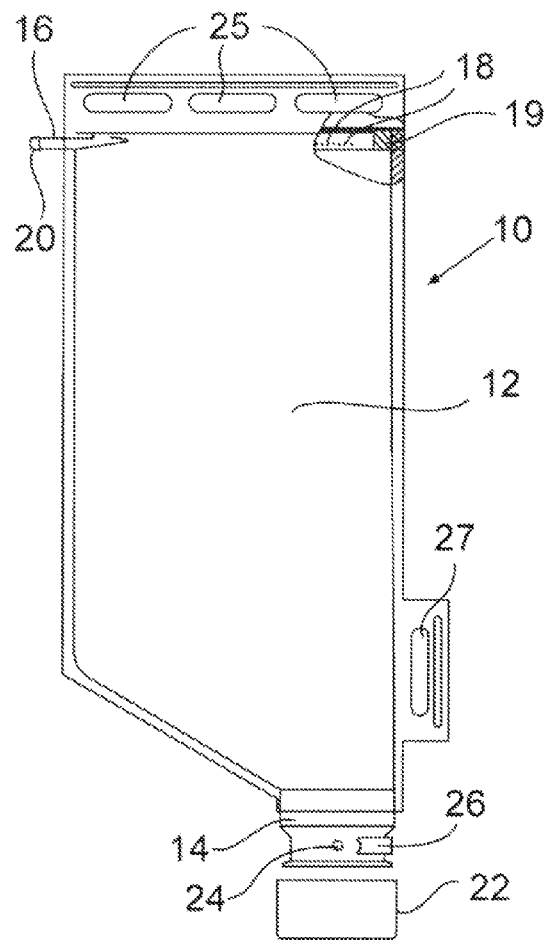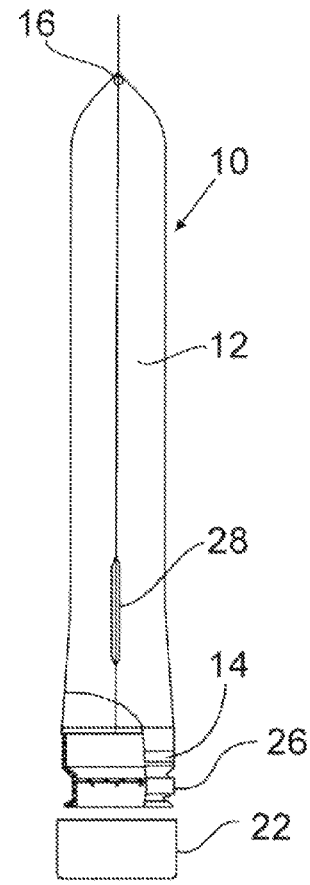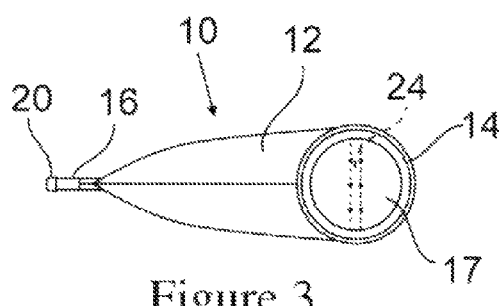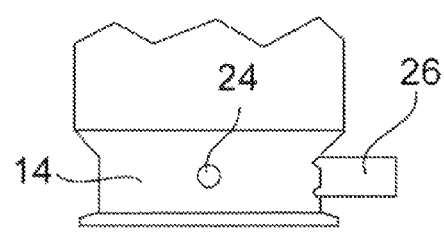
Figure 1
Figure 2
Figure 3
Figure 4

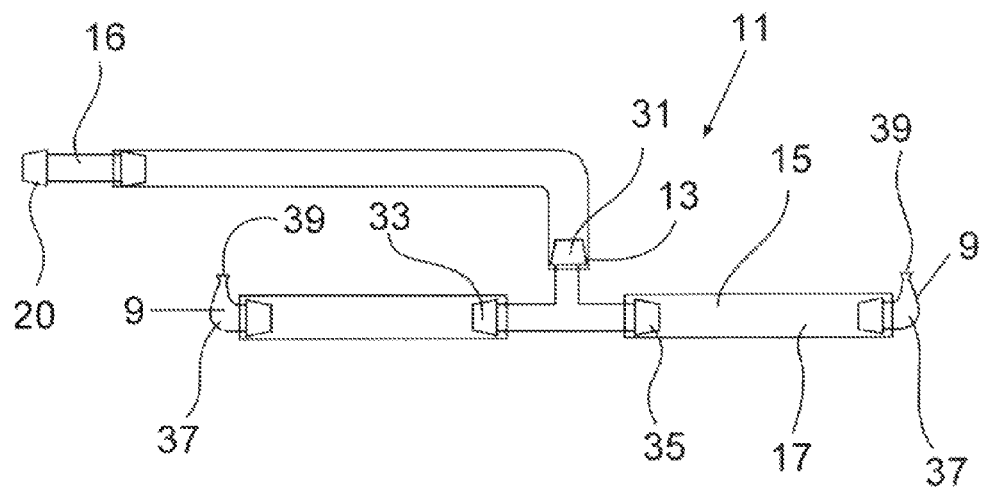
Figure 7
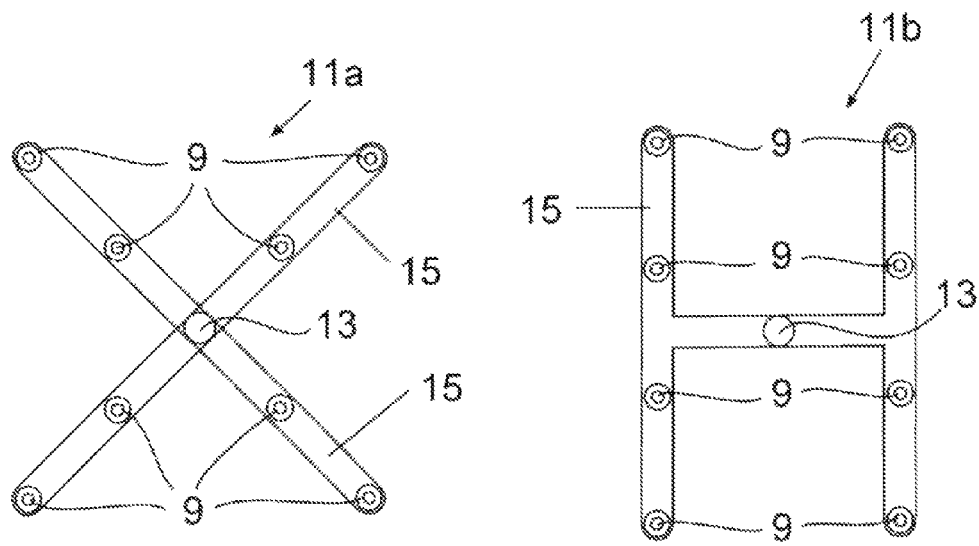
Figure 8
Figure 9

FEED BAG CONSTRUCTION

CROSS-REFERENCED RELATED APPLICATIONS

This application claims the benefit of U.S. Provisional Patent Application No. 61/283,930, filed on Dec. 9, 2009 and of U.S. Provisional Patent Application No. 61/271,667, filed on Jul. 24, 2009, the entire contents of which are incorporated by reference herein.

BACKGROUND OF THE INVENTION

This invention relates to a sterile conduit connection apparatus and more particularly to a feed-bag structure, that includes the sterile conduit connection apparatus.

Presently, a wide variety of solid compositions including cell culture supplements, buffers, media or the like are utilized in the biotechnology industry in producing and purifying biological products such as protein. These biological products are required to be produced under conditions to avoid product contamination. In many cases, the reagents are expensive and reagent losses should be minimized or prevented.

Presently, feed-bags containing the product producing reagents are provided with a conduit for filling and emptying the feed-bag of the reagent. This conduit is provided with a valve to permit or prevent passage of reagent through the conduit. The feed-bag conduit has a flange extending about the periphery of the conduit opening. A cap shaped to fit over the conduit opening to prevent outside atmosphere from entering the bag and for minimizing loss of reagent also is provided. A flexible gasket is positioned between the conduit flange and the cap. The cap also is provided with a flange that extends about its periphery. The flanges then are pressed together with the gasket between them by a clamp that extends over both flanges. The clamp has a pivot connection, which permits it to open and close about the flanges. This presently available conduit seal structure is undesirable since it is costly due to the multiple components and it requires two persons to effect the seal, one to activate the clamp and a second to retain the cap and conduit.

Presently available feed-bags also are provided with a means to connect to a source of water in order to wash out all available reagents to direct it to a desired point of use. Presently available washing arrangements are undesirable since not all of the reagent is washed out.

Accordingly, it would be desirable to provide a one-piece conduit sealing construction, which is effective and simple to operate by one person. In addition, it would be desirable to provide such a sealing arrangement, which permits storage of a means for opening or closing a valve within the conduit. Such a sealing construction would be economical and simple to operate. In addition, it would be desirable to provide a feed-bag structure that permits washing out of all of the reagent in the bag.

SUMMARY OF THE INVENTION

In accordance with this invention, a feed bag construction is provided for delivering solid or liquid reagents to a desired point of use such as to a cell culture medium or the like. The feed bag construction includes a bag sized to store a desired amount of reagent, a first conduit for filling or emptying the bag, a valve positioned within the first conduit for controlling passage of reagent through the conduit and a second conduit for introducing wash liquid into the bag to remove, by rinsing, residual reagent from the bag through the first conduit.

The second conduit comprises a connector arrangement for connection to a wash liquid source. In one aspect of this invention, the second conduit has multiple outlets for washing the interior of the bag to remove residual reagent therefrom is provided.

In another aspect of the present invention, the second conduit has a plurality of port sprayers for delivering the wash liquid to the interior of the bag. The port sprayers direct wash liquid to the top interior surface of the bag and to then direct wash liquid over the entire length of the bag interior and out through the first conduit.

The bag and first conduit are joined together in any conventional manner such as by heat sealing or with a clamp or the like. A cap is provided over the first conduit for retaining reagent within the bag such as when transporting the feed bag construction to a desired point of use. The cap is one piece thus providing a cost advantage and use advantage over the conduit closing means of the prior art. The one piece cap of this invention encloses a flange at the end of the conduit, prevents the valve from activating and provides a means for sealing the bag.

BRIEF DESCRIPTION OF THE DRAWINGS

FIG. 1 is a front exploded partial cross sectional of the feed bag construction of this invention.

FIG. 2 is a side exploded partial cross sectional view of the feed bag construction of FIG. 1.

FIG. 3 is a bottom isometric view of the feed bag construction of FIGS. 1 and 2 without the cap.

FIG. 4 is a partial side view of the first conduit of the feed bag construction of this invention showing a lever in a position for use to manipulate the butterfly valve in the first conduit.

FIG. 7 is a side partial cross sectional view showing the second conduit of this invention.

FIG. 8 is a top view of an alternative second conduit of this invention.

FIG. 9 is a top view of an alternative second conduit of this invention.

DESCRIPTION OF SPECIFIC EMBODIMENTS

Figure 5:
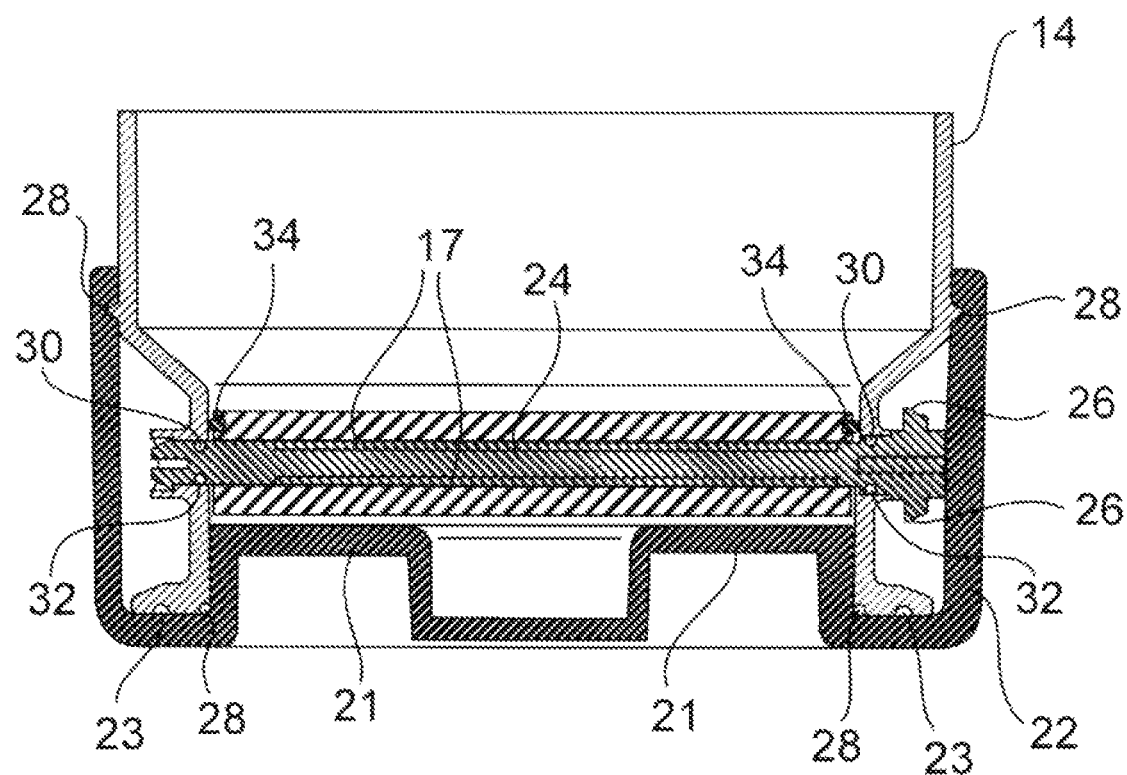
FIG. 5 is a cross sectional view of the cap utilized in the feed bag construction of this invention.

The feed bag construction of this invention is useful for storing and delivering liquid or solid reagents such as powder or tablets. Representative suitable reagents include cell culture supplements, buffers reagents, alkaline reagents, acidic reagents or the like. The feed bag construction of this invention permits opening or closing a conduit that can be an inlet or outlet utilized by one person and without the use of a clamping mechanism. The feed bag construction of this invention is disposable.

Referring to FIGS. 1, 2 and 3, the feed bag construction 10 of this invention is shown. The feed bag construction 10 includes a bag 12, a first conduit 14 sealed to the bag 10 and a second conduit 16. The bag 12 is formed of a flexible polymeric composition such as silicone, polyethylene, polypropylene, PTFE resin, C-Flex® resin or the like and laminates and co-extrusions of multilayers of these materials such as Pureflex™ films available from Millipore Corporation and HyQ® films available from Thermo Fisher Scientific Inc. The first conduit 14 is utilized to fill and empty the bag 12 with a desired reagent. A butterfly valve 17 is positioned within conduit 14 and is sized to open or close the conduit 14. The valve 17 is mounted on a shaft 24 and is connected to a lever 26. As shown in FIG. 4, the lever 26 can be pivoted to extend away from the conduit 14. The lever 26 is used to effect rotation of the valve 17 about shaft 24 thereby to open or close conduit 14. It is to be understood that any conventional means for pivoting the valve 17 can be utilized other than the lever 26 such as a hand operated knob or the like.

The bag 12 is provided with openings 25 to permit hanging the bag 12 during use. The bag 12 also is provided with a handle 27, which permits carrying the feed bag construction 10.

In use, the cap 22 is removed from the conduit 14 such as by unscrewing the cap. The cap can be removably connected to a conduit 14 by any conventional means such as by being snap fitted thereto. The lever 26 is exposed and is pivoted away from the conduit 14 thereby to provide leverage to the user so that the valve 17 connected to lever 26 can be pivoted about shaft 24 to render the conduit 14 open or closed. When the conduit 14 is opened, the bag 12 can be filled with or emptied of reagent passing through the conduit 14. Upon emptying the bag 12, wash liquid is supplied to conduit 16 through connector 20 and passed through outlets 18 thereby to remove stored reagent from the bag.

The second conduit 16 is sealed to the bag 12 and in a preferred embodiment has a plurality of outlets 18. The conduit 16 has a connector 20 adapted to be connected to a source of wash liquid such as sterile water. Alternatively, it may also be connected to a sterile connector system such as a Lynx® STS connector so that the bag can be presterilized in a sealed manner and then connected to a fluid source later on and still maintain its sterility inside the bag 12. The other end 19 of the conduit 16 is preferably sealed or contains an outlet 18. The end maybe sealed with a cap or plug (not shown) when the conduit is in the form of a preformed tube. It may also be sealed to itself or crimped shut.

The conduit 16 may be a tube made from commonly used materials such as silicone, polyethylene, polypropylene, C-Flex® material and the like.

Alternatively, it may be made of the same material as the bag and it may be formed if desired by a portion of the film that forms the bag. For example, it may be a separate piece of film that is folded/rolled on itself. One end 19 of the folded film is sealed such as onto itself to prevent flow. The other end is sealed to the connector in a liquid tight manner such as by adhesives, heat bonding, ultrasonic welding or clamps or cable ties. The connector 20/conduit 16 are then attached to the top seam or side of the bag 12 such as by adhesives, heat bonding, ultrasonic welding. In another embodiment, the conduit 16 is a portion of the film forming one side of the bag 12 and it is folded back on itself, sealed and attached as described above.

In a further embodiment the conduit is formed of a porous material such as a non-woven plastic paper such as Typar® or Tyvek® paper, folded/rolled to form the conduit 16 and sealed and attached to the bag 12 in a manner similar to that described above.

The conduit 16 preferably has a series of outlets 18 as shown along the length of the conduit to distribute the flow of wash liquid across the width of the bag 12. Preferably the flow is even across the width of the bag 12. The outlets size may vary depending upon the size of the stream/rate of flow that is desired. The outlet size should be large enough to ensure that there is good washing of the material contained within the bag 12 during the washing procedure with the minimal amount of fluid necessary. If desired the outlets 18 may vary in size along the length of the conduit 16 such as from smaller near the connector 20 to larger near the other end 19 of the conduit 16 so as to ensure that liquid is evenly distributed across the length of the conduit 16 as flow and pressure drops along the length of the conduit 16.

The outlets 18 may also be arranged in a single row or multiple rows along the length of the conduit 16 as desired. In a single row embodiment, the outlets 18 may all be uniformly directed downward into the bag 12. Alternatively, they may alternate in series such that a first outlet 18 is directed downwardly toward a first side of the bag 12 and a second outlet is directed downwardly and toward the second side of the bag. Another embodiment would have a third outlet 18 directed directly down into the bag 12. In a multiple row embodiment, one row of outlets 18 would be directed downwardly toward a first side of the bag 12 and a second row of outlets 18 outlet is directed downwardly and toward the second side of the bag. Another embodiment would have a third row of outlets 18 directed directly down into the bag 12.

The conduit 16 either directly or through a sterile connector described above is connected to a source of wash liquid such as sterile water, a sterile buffer solution such as phosphate buffer and the like or whatever other liquid, such as a solvent, is used with the powder.

FIGS. 6-9 shows a feed bag with a second embodiment of the second conduit 11 of the present invention.

Referring to Figures and 7, the second conduit 11 comprises a connector 20 secured to inlet conduit 16 which, in turn is connected to connecting conduits 13 and 15 with barb connectors 31, 33 and 35. Of course other connectors can be used in lieu of the hose barbs such as threaded connections, such as male/female threaded hose connections (not shown), speed connections (not shown) that use various ball bearing and sliding locking mechanisms to hold the male and female connectors together, overmolded hose and T connectors (not shown) such as are available from Saint Gobain Performance Plastics of Worcester, Mass. and the like. The port sprayer 9 preferably includes a tapered wall 37 which tapers toward exit port 39. The use of the tapered wall 37 permits wash liquid to exit port sprayer 9 under high enough pressure so that the wash liquid contacts the top interior surface 18 of the bag 12. The construction shown in FIG. 7 permits complete removal of reagent from the bag 12. It is to be understood that other wall designs such as a straight wall can be utilized. The sprayer 9 may have one opening or more than one opening as desired to provide the desired spray effect. Alternatively, the sprayer may have a spray ball design if desired.

Figure 6:
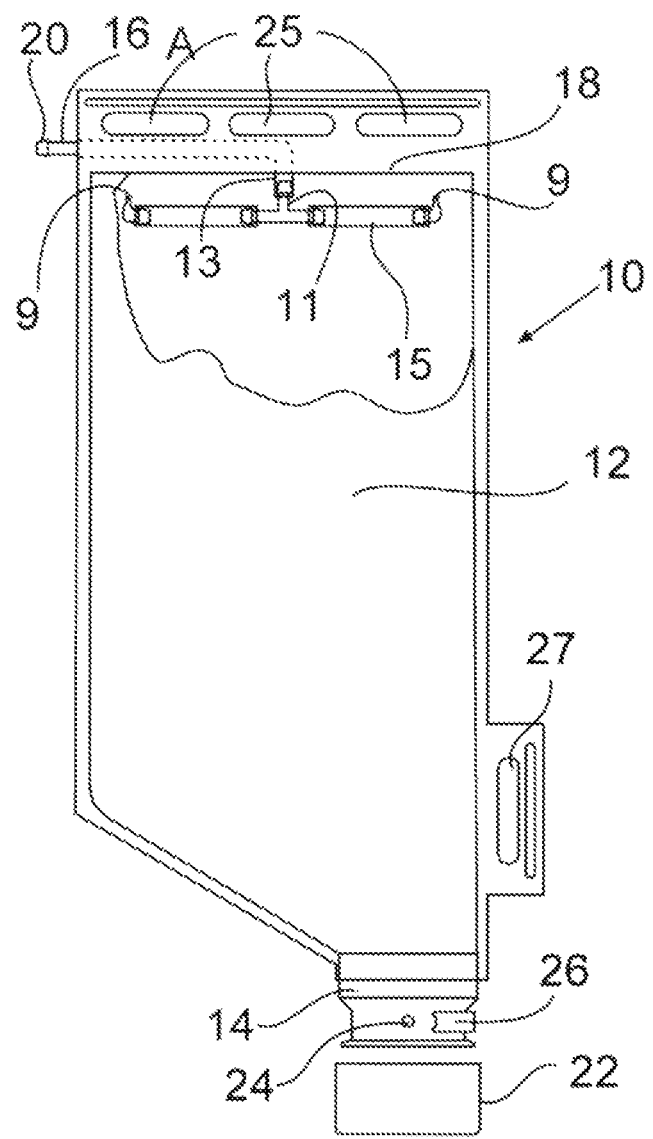
FIG. 6 is a cross sectional view of the feed bag construction of a second embodiment of the present invention.

Referring to FIG. 6, the second conduit construction 11 is shown in an I shape with connecting conduits 13, 15 and a plurality of port sprayers 9 is shown.

Referring to FIG. 8, an alternative second conduit construction 11a is shown in an X shape with connecting conduits 13, 15 and a plurality of port sprayers 9 is shown.

Referring to FIG. 9 an alternative second conduit construction is shown in an H shape with connecting conduits 13,15 and a plurality of port sprayers 9.

A cap 22 is provided which fits over conduit 14 thereby to prevent leakage through conduit 14. The cap 22 fits over the lever 26. Referring to FIG. 5, the cap 22 has threads 28, which permit screwing the cap 22 onto conduit 14. Valve 17 is shown mounted on shaft 24. Lever 26 is connected to shaft 24 and is nested within cap 22. O ring 28 mounted in cap 22 seals the end of conduit 14 to cap 22. O rings 30 and 32 seal the shaft 24 to valve 17. O ring 34 seals the valve 17 to conduit 14. The cap 22 is provided with one or more raised sections 21. The raised sections 21 prevent activation of the valve 17 when the cap is in position on the conduit 14. The one piece cap encloses the end of the conduit 14, the valve 17 and the lever 26 and can be removed from or attached to conduit 14 by one person. The O ring 28 can be molded to the end of conduit 14, the inside surface of the cap 28 or can be a separate piece. The end of the conduit 14 can be provided with an optional groove 23, which is adapted to house an additional gasket.

What is claimed:

1. A feed bag construction consisting essentially of a bag sized to store a desired amount of powder reagent, a first conduit formed at a first lowermost end of the bag, the first conduit being used to empty the bag of contents, a valve positioned within the first conduit for controlling passage of powder reagent through the first conduit, the valve being mounted on a shaft and connected to a lever, the lever being capable of being pivoted to extend away from the first conduit during use, the lever effecting rotation of the valve about shaft thereby to selectively open or close the first conduit, a cap enclosing the first conduit, valve and lever when pivoted toward the first conduit, and a second conduit located at and sealed to a second end of the bag opposite the first end of the bag for introducing wash liquid into the bag to remove, by rinsing, residual powder reagent from the bag through the first conduit, the second conduit extending across the length of the second end of the bag, the second conduit having a connector positioned outside the feed bag on one side of the second conduit and a seal adjacent another side of the second conduit, the second conduit having multiple outlets spaced along its length, and the bag being asymmetrical in shape having a first lateral side wall, the first lateral side wall extending vertically between the conduit on the first end of the bag to the second end of the bag and a second lateral side wall opposite the first lateral side wall, the second lateral side wall having a tapered portion extending outwardly at an angle from the first conduit and a second portion extending vertically between an end of the tapered portion farthest from the first conduit and the second end of the bag.

2. A feed bag construction consisting essentially of a bag sized to store a desired amount of powder reagent, a first conduit formed at a first lowermost end of the bag, the first conduit being used to empty the bag of contents, a valve positioned within the first conduit for selectively controlling passage of powder reagent through the first conduit, the valve being mounted on a shaft and connected to a lever, the lever being capable of being pivoted to extend away from the conduit during use, the lever effecting rotation of the valve about shaft thereby to selectively open or close the first conduit a cap enclosing the first conduit, valve and lever when pivoted toward the first conduit, and a second conduit located at and sealed to a second end of the bag opposite the first end of the bag for introducing wash liquid into the bag to remove, by rinsing, residual powder reagent from the bag through the first conduit, the second conduit extending across the length of the second end of the bag, the second conduit having a connector positioned outside the feed bag on one side of the conduit and a seal adjacent another side of the conduit, the second conduit having multiple outlets spaced along its length, and the bag being asymmetrical in shape having a first lateral side wall, the first lateral side wall extending vertically between the conduit on the first end of the bag to the second end of the bag and a second lateral side wall opposite the first lateral side wall, the second lateral side wall having a tapered portion extending outwardly at an angle from the first conduit and a second portion extending vertically between an end of the tapered portion farthest from the first conduit and the second end of the bag.

\* \* \* \* \*